(12) United States Patent
Suijver et al.

(10) Patent No.: US 9,176,276 B2
(45) Date of Patent: Nov. 3, 2015

(54) IMAGING SYSTEM FOR THREE-DIMENSIONAL IMAGING OF THE INTERIOR OF AN OBJECT

(75) Inventors: Freek Suijver, Dommelen (NL); Benno Hendriks, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1932 days.

(21) Appl. No.: 12/299,688

(22) PCT Filed: May 2, 2007

(86) PCT No.: PCT/IB2007/051631
§ 371 (c)(1),
(2), (4) Date: Aug. 5, 2009

(87) PCT Pub. No.: WO2007/132378
PCT Pub. Date: Nov. 22, 2007

(65) Prior Publication Data
US 2010/0048995 A1    Feb. 25, 2010

(30) Foreign Application Priority Data

May 9, 2006 (EP) ..................................... 06113712

(51) Int. Cl.
*A61B 1/06* (2006.01)
*G02B 6/04* (2006.01)
(Continued)

(52) U.S. Cl.
CPC .............. *G02B 6/04* (2013.01); *A61B 1/00167* (2013.01); *A61B 1/00193* (2013.01); *G02B 6/0008* (2013.01)

(58) Field of Classification Search
CPC ........ A61B 1/00; A61B 1/06; A61B 1/00163; A61B 1/00167; A61B 1/0017; A61B 1/00172; A61B 1/07; A61B 1/00165

USPC .......... 600/166, 160, 173, 182; 362/554, 574, 362/556; 385/115, 116–118
See application file for complete search history.

(56) References Cited

U.S. PATENT DOCUMENTS 4,656,508 A    4/1987    Yokota
4,924,853 A    5/1990    Jones, Jr. et al.
(Continued)

FOREIGN PATENT DOCUMENTS

EP    1371321 A1    12/2003
FR    2783330 A1    3/2000
(Continued)

OTHER PUBLICATIONS

R. Zhang: et al: "Shape from Shading: A Survey" IEEE Transactions on Pattern Analysis and Machine Intelligence, vol. 21, No. 8, Aug. 1999, pp. 690-706, XP002452732.

*Primary Examiner* — John P Leubecker
*Assistant Examiner* — Arnaldo Torres Diaz

(57) ABSTRACT

The invention relates to an imaging system and a method for three-dimensional imaging of the interior of an object. The imaging system comprises illumination means (10), detection means (11) and reconstruction means. The illumination means is adapted to illuminate the interior of the object with light, wherein the illumination means (10) is capable of generating different spatial light intensity distributions on the interior of the object. The detection means (11) is adapted to detect the different spatial light intensity distributions, and the reconstruction means is adapted to reconstruct a three-dimensional image from the detected different spatial light intensity distributions. The invention relates further to an optical fiber system comprising a transfer mechanism to transfer the optical fiber system from a first condition, in which optical fibers diverge from each other, to a second condition, in which optical fibers are parallel to each other, and vice versa.

14 Claims, 5 Drawing Sheets

(51) Int. Cl.
*A61B 1/00* (2006.01)
*F21V 8/00* (2006.01)

(56) References Cited

U.S. PATENT DOCUMENTS

| | | | |
|---|---|---|---|
| 5,200,838 A | | 4/1993 | Nudelman et al. |
| 5,305,759 A | | 4/1994 | Kaneko et al. |
| 5,432,543 A | | 7/1995 | Hasegawa et al. |
| 5,436,655 A | * | 7/1995 | Hiyama et al. ............... 348/45 |
| 5,575,751 A | * | 11/1996 | Walther et al. ............. 600/104 |
| 5,577,991 A | | 11/1996 | Akui et al. |
| 5,823,942 A | * | 10/1998 | Toida ........................... 600/160 |
| RE36,434 E | * | 12/1999 | Hamlin et al. ............... 600/109 |
| 6,066,090 A | | 5/2000 | Yoon |
| 6,485,413 B1 | * | 11/2002 | Boppart et al. ............. 600/160 |
| 6,563,105 B2 | | 5/2003 | Seibel |
| 6,768,918 B2 | * | 7/2004 | Zelenchuk ................... 600/476 |
| 7,006,220 B2 | * | 2/2006 | Bambot et al. .............. 356/338 |
| 7,127,282 B2 | * | 10/2006 | Nordstrom et al. ......... 600/477 |
| 7,282,723 B2 | * | 10/2007 | Schomacker et al. ..... 250/458.1 |
| 7,344,528 B1 | * | 3/2008 | Tu et al. ......................... 606/7 |
| 8,005,527 B2 | * | 8/2011 | Zelenchuk ................... 600/407 |
| 2001/0029316 A1 | * | 10/2001 | Webb ........................... 600/113 |
| 2002/0082474 A1 | | 6/2002 | Yamamoto |
| 2002/0168158 A1 | * | 11/2002 | Furusawa et al. ........... 385/116 |
| 2002/0190212 A1 | * | 12/2002 | Boas et al. ................... 250/341.1 |
| 2003/0130562 A1 | * | 7/2003 | Barbato et al. .............. 600/109 |
| 2003/0174208 A1 | | 9/2003 | Glukhovsky |
| 2004/0147808 A1 | * | 7/2004 | MacAulay et al. ........... 600/160 |
| 2004/0220453 A1 | * | 11/2004 | Jones et al. ................... 600/160 |
| 2005/0015006 A1 | | 1/2005 | Mitschke et al. |
| 2005/0090733 A1 | | 4/2005 | Van Der Lugt et al. |
| 2006/0009690 A1 | | 1/2006 | Fuimaono et al. |
| 2006/0149134 A1 | * | 7/2006 | Soper et al. ................... 600/182 |
| 2007/0013710 A1 | * | 1/2007 | Higgins et al. ............... 345/581 |
| 2007/0015969 A1 | * | 1/2007 | Feldman et al. ............. 600/160 |
| 2007/0073104 A1 | * | 3/2007 | Iketani et al. ................ 600/109 |
| 2007/0161854 A1 | * | 7/2007 | Alamaro et al. ............. 600/109 |
| 2007/0238930 A1 | * | 10/2007 | Wiklof et al. ................ 600/160 |
| 2007/0244364 A1 | * | 10/2007 | Luanava et al. ............. 600/160 |
| 2007/0244365 A1 | * | 10/2007 | Wiklof .......................... 600/173 |
| 2007/0276187 A1 | * | 11/2007 | Wiklof et al. ................ 600/182 |
| 2008/0004495 A1 | * | 1/2008 | Allen et al. ................... 600/160 |
| 2008/0097150 A1 | * | 4/2008 | Hasegawa et al. ........... 600/109 |
| 2008/0262359 A1 | * | 10/2008 | Tearney et al. .............. 600/476 |
| 2009/0012369 A1 | * | 1/2009 | Robinson et al. ............ 600/182 |
| 2010/0280321 A1 | * | 11/2010 | Modell ......................... 600/160 |

FOREIGN PATENT DOCUMENTS

| | | |
|---|---|---|
| GB | 2342524 A | 4/2000 |
| JP | 10043127 A | 2/1998 |
| JP | 63242233 A | 10/1998 |
| JP | 2004045322 A | 2/2004 |
| JP | 2005-034654 A | 2/2005 |
| WO | 8911252 A1 | 11/1989 |
| WO | 2005077272 A1 | 8/2005 |

* cited by examiner

IMAGING SYSTEM FOR THREE-DIMENSIONAL IMAGING OF THE INTERIOR OF AN OBJECT

BACKGROUND

The invention relates to an imaging system for three-dimensional imaging of the interior of an object. The invention relates further to an optical fiber system for the use in the imaging system, and to a method for three-dimensional imaging of the interior of an object.

In particular in the field of minimally invasive surgery, it is important that high quality images of the interior of an object which has to be treated, e.g. bladder, are provided for the surgeon to ensure that surgical instruments can be advanced and used within the object accurately.

It is known that an image of the interior of the object is transferred via an optical fiber from the tip of an endoscope to a monitor on which the surgeon can observe the interior of the object during a surgical procedure. But this image is only a two-dimensional image which does not comprise depth information which is important for an accurate advancement and use of surgical instruments within the object.

The U.S. Pat. No. 6,066,090 discloses a branched endoscope system wherein each branch of the endoscope is adapted to acquire an image of the interior of the object and to transfer it to a monitor on which the surgeon can simultaneously view the images of the different branches. Also by using this branched endoscope system only two-dimensional images are shown, and a depth information of the interior of the object is not provided.

The U.S. Pat. No. 5,577,991 discloses an endoscope having two cameras. Based on the parallax difference from the two images a three-dimensional reconstruction of the image is created. This endoscope provides depth information, but it is bulky limiting the usefulness for imaging in the interior of an object.

SUMMARY

It is therefore the object of the invention to provide an imaging system which can provide depth information of the interior of an object and which is smaller than known imaging systems for imaging the interior of the object.

This object is achieved by an imaging system for three-dimensional imaging of the interior of an object comprising:
illumination means being adapted to illuminate the interior of the object with light, wherein the illumination means is capable of generating different spatial light intensity distributions on the interior of the object,
detection means being adapted to detect the different spatial light intensity distributions,
reconstruction means being adapted to reconstruct a three-dimensional image from the detected different spatial light intensity distributions.

The imaging system according to the invention is capable of generating different spatial light intensity distributions on the interior of the object. The generation of different spatial light intensity distributions can easily be performed with illumination means, for example, by illuminating the interior of the object in different directions. Furthermore, the illumination means according to the invention can be constructed smaller than known imaging systems, which image the interior of the object and which provide depth information.

It is preferred that the detection means comprises one single detector and/or one single collector. In accordance with the invention, this single detector can be a camera located on a tip of an endoscope. Furthermore, the single collector can be an optical fiber bundle, which is located within an endoscope and which is connected with a detector such that the optical fiber bundle of the detector means collects light of the interior of the object and transfers it to the detector. The use of only one detector and/or only one collector, for example, the use of only one camera on the tip of an endoscope or only one optical fiber bundle, leads to a miniaturization of the imaging system according to the invention. Thus, in comparison to known imaging systems, the insertion into an endoscope and the use within the interior of an object is facilitated.

It is further preferred that the reconstruction means is adapted to reconstruct a three-dimensional image from the detected different spatial light intensity distributions by shape-from-shading. By shape-from-shading three-dimensional images of high quality can be reconstructed from the detected light.

It is further preferred that the illumination means is adapted to illuminate the interior of the object from different directions to generate different spatial light intensity distributions on the interior of the object. It is further preferred that the illumination means is adapted to illuminate the interior of the object from different directions to generate different spatial light intensity distributions on the interior of the object, wherein different spatial light intensity distributions are collected by only one detector and/or one collector.

This arrangement has the advantage that the interior of the object can easily be illuminated with different spatial light intensity distributions. Furthermore, with this arrangement different light intensity distributions of light, which has been reflected from the interior of the object, can be detected comprising different shading patterns which can be used to reconstruct a three-dimensional image by shape-from-shading in an efficient way.

In an embodiment, the illumination means comprises one illuminator which is moveable to illuminate the interior of the object from different directions to generate different spatial light intensity distributions on the interior of the object. In particular, the one illuminator is moveable relative to the detection means. The illuminator is preferentially the end portion of an optical fiber or of an optical fiber bundle. Since, in this embodiment, only one illuminator is used, the imaging system is further miniaturized facilitating the insertion into an endoscope and into the interior of an object.

In a further embodiment, the illumination means comprises several illuminators to illuminate the interior of the object from different directions to generate different spatial light intensity distributions on the interior of the object. With this arrangement different spatial light distributions can easily be generated on the interior of the object.

In an embodiment, these illuminators are moveable. This increases the number of directions from which the interior of the object can be illuminated.

If, in an embodiment, the illumination means comprises several illuminators and the detection means comprises several collectors and/or detectors, each illuminator and/or collector and/or detector can be individually addressable in order to allow to generate different spatial light intensity distributions on the interior of the object and to detect the different light intensity distributions which have been reflected from the interior of the object.

In an embodiment according to the invention, the illumination means comprises at least one optical fiber and a light source, wherein the detection means comprises at least one optical fiber and a detector, and wherein the optical fibers are arranged within a casing, in particular a casing of an endoscope, to transfer light from the light source to the interior of the object and to transfer light, which has been reflected from the interior, to the detector. This use of optical fibers, a light source and a detector provides a simple arrangement of the imaging system, which can be easily assembled.

It is preferred that the illumination means comprises several optical fibers which are adaptable to illuminate the interior of the object from different directions to generate different spatial light intensity distributions on the interior of the object. By using this illumination on the interior of the object different spatial light distributions can easily be generated.

It is further preferred that the detection means comprises only one optical fiber or one optical fiber bundle to collect the light from the several optical fibers of the illumination means to detect different spatial light intensity distributions which have been reflected from the interior of the object. Also by using this arrangement different spatial light intensity distributions, which have been reflected from the interior of the object, can easily be detected. Furthermore, the detected different light intensity distributions acquired with this arrangement can be used to reconstruct a three-dimensional image by shape-from-shading with low computation effort.

It is further preferred that the illumination means comprises one illuminator comprising a light source and an optical fiber or a bundle of optical fibers, wherein the optical fiber or the bundle of optical fibers is moveable to illuminate the interior of the object from different directions to generate different spatial light intensity distributions on the interior of the object. In particular, the optical fiber or the bundle of optical fibers of the illuminator is moveable with respect to the at least one optical fiber of the detection means. It is further preferred that the detector means comprises only one optical fiber or only one optical fiber bundle for collecting different spatial light intensity distributions reflected from the interior of the object and only one optical fiber or one optical fiber bundle for illuminating the interior of the object, wherein the only one optical fiber or one optical fiber bundle for illuminating the interior of the object is moveable with respect to the only one optical fiber or one optical fiber bundle for detecting different light intensity distributions. Since only one illuminator is used, the construction of the imaging system becomes less complex.

It is preferred, that the optical fibers of the illumination means and of the detection means are located within the same casing. The casing is preferentially a casing of an endoscope. The casing can be rigid or flexible. This reduces the number of casings which have to be used, wherein the insertion of a casing into the object, for example, into a bladder, is simplified and the space occupied by the casing is reduced facilitating the movement and operation of the casing and, for example, of further surgical instruments within the object.

The optical fibers of the illumination means and the detection means can be arranged to generate different spatial light intensity distributions on the interior of the object, and to detect light which has been reflected from the interior of the object. As already explained above, the detected different light intensity distributions acquired with this arrangement can be used to reconstruct a three-dimensional image by shape-from-shading with low computation effort. The use of optical fibers for this kind of acquisition enables a compact and space-saving construction of the imaging system.

The imaging system can comprise an optical fiber system, which comprises a bundle of the optical fibers of the illumination means and/or of the detection means and i) a first condition in which the optical fibers are arranged such that at least two of the optical fibers diverge from each other at an end portion of the bundle, and ii) a second condition in which the optical fibers are arranged such that the optical fibers are parallel to each other at said end portion of the bundle, wherein the optical fiber system comprises a transfer mechanism which is adapted to transfer the optical fiber system from one of the first and the second condition to the other of the first and the second condition. If the optical fiber system is in the second condition, in which the optical fibers are parallel to each other, the optical fiber system can easily be inserted into e.g. an endoscope facilitating the assembling of the imaging system, and the imaging system with the optical fiber system can easily be inserted into the interior of the object. After the optical fiber system has been inserted into e.g. an endoscope and/or after the imaging system has been inserted into the interior of the object, the optical fiber system can be transferred into the first condition, in which, since at least two optical fibers diverge from each other at an end portion of the bundle, at least two of the optical fibers illuminate the interior of the object from different directions, i.e. different spatial light intensity distributions are generated on the interior of the object. The different spatial light intensity distributions, which have been reflected from the interior of the object, are detected. Thus, this possibility of transferring from the first to the second condition and vice versa enables a simplified insertion into and take out from the interior of the object and facilitates the assembling of the imaging system.

It is preferred that the transfer mechanism is adapted to unfold the optical fibers at said end portion of the bundle to transfer the optical fiber system from the second condition to the first condition. The unfold procedure allows to transfer the optical fiber system from the second condition to the first condition in an effective way.

The transfer mechanism can also be adapted to fold the optical fibers at said end portion of the bundle to transfer the optical fiber system from the first condition to the second condition. The fold procedure allows to transfer the optical fiber system from the first to the second condition in an effective way.

It is further preferred that the optical fibers of the illumination means and of the detection means are arranged to a bundle, wherein the at least one optical fiber of the detection means is located in the center of the bundle and wherein the optical fibers of the illumination means surround the at least one optical fiber of the detection means.

By using such an arrangement, different spatial light intensity distributions are acquired, wherein the different spatial light intensity distributions are adapted to stabilize the reconstruction algorithm and to increase the accuracy of the reconstruction.

Each of the optical fibers of the illumination means and/or of the detection means can be individually addressable in order to allow to acquire different predetermined and/or preselected spatial light intensity distributions of the interior of the object.

It is preferred that the illumination means and the detection means are adapted to acquire different spatial light intensity distributions. In particular, this means, that the illumination direction and/or the collecting direction are different for different spatial light intensity distributions which have been acquired from different directions sequentially. Since by using this arrangement the illumination and collecting directions are known for each different spatial light intensity distribution, to each spatial light intensity distribution a direction, which can be used for the reconstruction of a three-dimensional image, can easily be assigned.

It is a further object of the invention to provide an optical fiber system which can easily be inserted into e.g. an endoscope to assemble the imaging system according to the invention and with which an imaging system provided with the optical fiber system can easily be inserted into the interior of an object, for example, into a bladder.

This object is achieved by an optical fiber system, in particular for the use in an imaging system for three-dimensional imaging of the interior of an object according to the invention, wherein the optical fiber system comprises a bundle of optical fibers and i) a first condition in which the optical fibers are arranged such that at least two of the optical fibers diverge from each other at an end portion of the bundle, and ii) a second condition in which the optical fibers are arranged such that the optical fibers are parallel to each other at said end portion of the bundle, wherein the optical fiber system comprises a transfer mechanism which is adapted to transfer the optical fiber system from one of the first and the second condition to the other of the first and the second condition. As already explained above, this optical fiber system can easily be inserted into e.g. an endoscope facilitating the assembling of an imaging system for three-dimensional imaging. Furthermore, an endoscope comprising this optical fiber system can easily be inserted in the interior of an object in the second condition, wherein, after the insertion has been completed, the optical fiber system can be transferred to the first condition allowing to illuminate the interior of the object and/or to collect light, which has been reflected and/or scattered from the interior of the object, in different directions.

It is preferred that the transfer mechanism is adapted to unfold the optical fibers at said end portion of the bundle to transfer the optical fiber system from the second condition to the first condition. The unfold procedure allows to transfer the optical fiber system from the second condition to the first condition in an effective way.

The transfer mechanism can also be adapted to fold the optical fibers at said end portion of the bundle to transfer the optical fiber system from the first condition to the second condition. The fold procedure allows to transfer the optical fiber system from the first to the second condition in an effective way.

It is a further object of the invention to provide an imaging method, which can provide depth information of the interior of an object and which can be performed by using an imaging system for three-dimensional imaging of the interior of an object which is smaller than known imaging systems.

This object is achieved by a method for three-dimensional imaging of the interior of an object comprising following steps:
  illuminating the interior of the object with light by illumination means, wherein different spatial light intensity distributions are generated on the interior of the object,
  detecting the different spatial light intensity distributions by detection means,
  reconstructing a three-dimensional image from the detected different spatial light intensity distributions by reconstruction means.

That is, on the interior of the object different spatial light intensity distributions are generated, e.g., the illumination means can comprise at least two illumination fiber bundles which illuminate the interior of the object from different directions.

As mentioned above, this method can easily be performed with illumination means. Furthermore, the imaging system, which is needed for the method according to the invention, can be constructed smaller than known imaging systems, which image the interior of the object and which provide depth information.

It is preferred that on the interior of the object different spatial light intensity distributions are sequentially generated. In particular this means, that the illumination direction and/or the collecting direction are sequentially modified. Since the illumination and collecting directions, i.e. the acquisition directions, are known for each detected spatial light intensity distribution, to each detected spatial light intensity distribution a direction, which can be used for the reconstruction of a three-dimensional image, can easily be assigned.

It is further preferred that the light is detected by one single detector and/or collected by one single collector. As already explained above, since only one single detector and/or collector is needed, the size of the imaging system can be reduced wherein the insertion of the imaging system into a casing and the insertion into the interior of an object are facilitated.

It is further preferred that a three-dimensional image is reconstructed from the detected different spatial light intensity distributions by shape-from-shading. By using shape-from-shading a three-dimensional image of high quality can be reconstructed.

BRIEF DESCRIPTION OF THE DRAWINGS

The invention will in the following be explained with respect to illustrative embodiments in combination with a drawing, in which.

DETAILED DESCRIPTION

Figure 1:
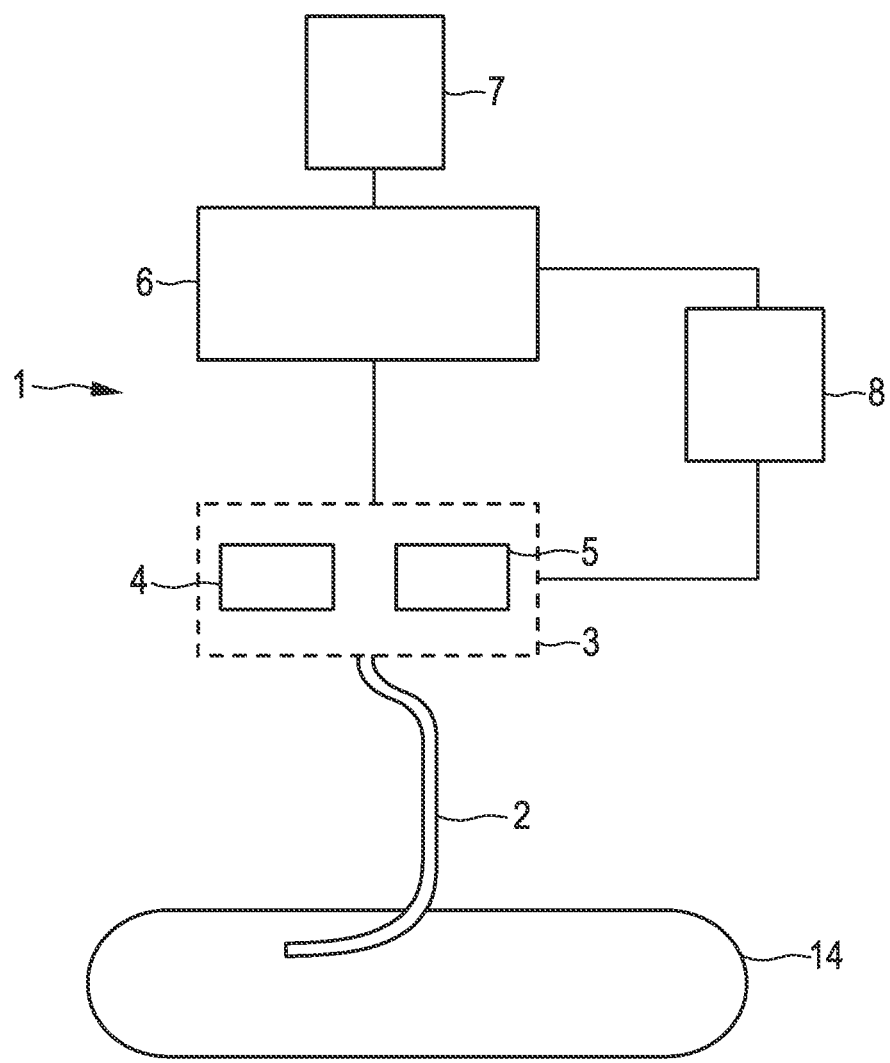
FIG. 1 shows schematically an embodiment of an imaging system for three-dimensional imaging of the interior of an object according to the invention.

FIG. 1 shows schematically an imaging system 1 for three-dimensional imaging of the interior of an object. The imaging system 1 comprises an endoscope 2 which is inserted into a human body 14, for example, into a bladder. The endoscope 2 is connected to an operational unit 3 comprising a light source 4 and a detector 5.

Figure 2:
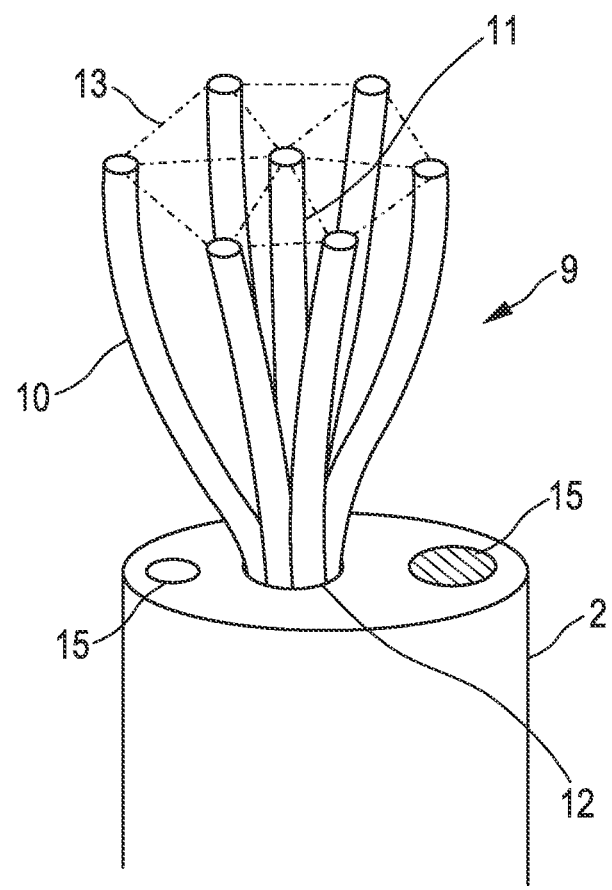
FIG. 2 shows the tip of an endoscope of the embodiment of FIG. 1 comprising an optical fiber system according to the invention in a first condition.

The light source 4 preferentially emits light in the visible range. The light of the light source 4 is coupled into at least one illumination fiber bundle 10. In this embodiment, the light of the light source 4 is coupled into several illumination fiber bundles 10, which are shown in FIG. 2 and which surround a central collecting fiber bundle 11.

Each of the fiber bundles 10, 11 comprises several optical fibers. In another embodiment according to the invention, instead of the fiber bundles 10, 11, optical fibers with a diameter corresponding to the diameter of the fiber bundles can be used, respectively, for example, one collecting optical fiber which is surrounded by several illumination optical fibers. In another embodiment according to the invention, the imaging system comprises several illumination optical fibers which surround one collecting optical fiber bundle. The optical fiber bundle comprises, for example, 10,000 single optical fibers.

Light of the light source 4 is transferred via the illumination fiber bundles 10 into the interior of the object 14 which has to be imaged. Light, which is reflected from the interior of the object is collected by the collecting fiber bundle 11 wherein, since the interior of the object 14 is illuminated from different directions by the illumination fiber bundles 10, on the interior of the object different spatial light intensity distributions are generated. The detected light is transferred via the collecting fiber bundle 11 to the detector 5. The detector 5 is preferentially a CCD camera, which converts the detected different spatial light intensity distributions into electrical signals. These electrical signals, i.e. the different spatial light intensity distributions, are transferred to the reconstruction means 6 which is in this embodiment a reconstruction computer. The reconstruction computer is adapted to reconstruct a three-dimensional image from the interior of the object 14 from the different spatial light intensity distributions. The reconstruction of a three-dimensional image from different spatial light intensity distributions, which have been generated by illuminating the interior of the object from different directions and by detecting the light reflected from the interior of the object, is well known, for example, from "Shape from Shading: A Survey", Ruo Zhang, Ping-Sing Tsai, James Edwin Cryer and Mubarak Shah, IEEE Transactions on Pattern Analysis and Machine Intelligence, Vol. 21, No. 8, August 1999, pp. 690-706. It is preferred to use shape-from-shading to reconstruct a three-dimensional image from the collected light.

The reconstruction means 6 is connected to a monitor 7 which shows the reconstructed three-dimensional image of the interior of the object 14. Instead of the monitor 7 stereoscopic glasses or displays, which generate a three-dimensional impression, for example, for the surgeon, can be used.

The operational unit 3 and the reconstruction means 6 are connected to a control unit 8, which is preferentially a control computer and which controls the operational unit 3 and the reconstruction means 6.

FIG. 2 shows an optical system 9 comprising several illumination fiber bundles 10 and one collecting fiber bundle 11 in a first condition in which the fiber bundle diverge from each other starting from a position outside of the casing 2 in which the fiber bundles 10, 11 have been inserted. The fiber bundles 10, 11 are inserted into an optical system insertion hole 12 in the endoscope 2. The endoscope 2 comprises further insertion holes 15, in which, for example, surgical instruments can be located, in order to enable a surgeon to reconstruct and view three-dimensional images of the interior of the object 14 during a surgical procedure.

In another embodiment, in one of the insertion holes 15 an optical fiber or an optical fiber bundle can be inserted to collect light from the interior of the object, thereby collecting different spatial intensity distributions from the interior of the object. In this other embodiment, all or some of the fiber bundles 10, 11 are connected to the light source 4 to illuminate the interior of the object in different directions.

FIG. 2 shows the end portion of the endoscope 2 and of the optical system 9 which has been inserted into the object 14. In FIG. 2, the optical fiber system 9 is shown in a second condition, which is used during the imaging procedure. Since the illumination fiber bundles 10 diverge from each other, they illuminate the interior of the object 14 in different directions, and thus, the reflected light is collected from the collecting fiber bundle 11 from different directions. Therefore, by using the optical fiber system 9 in the first condition each illumination fiber bundle illuminates the interior of the object in a different direction, wherein each illumination fiber generates another spatial light intensity distribution on the interior of the object.

Figure 3:
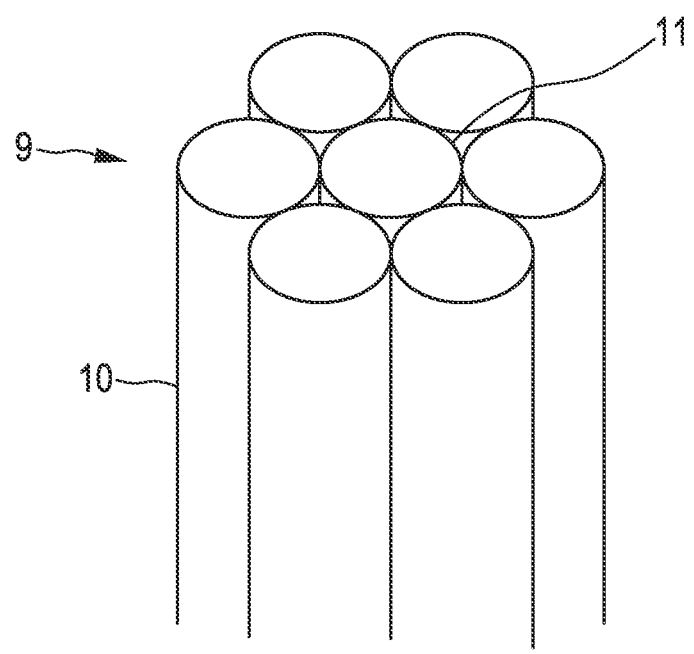
FIG. 3 shows the optical fiber system in a second condition.

FIG. 3 shows the end portion of the optical fiber system 9, which has been inserted into the object, in a first condition, in which the illumination fiber bundles 10 and the collecting fiber bundle 11 are arranged parallel to each other. The first condition of the optical fiber system 9 is used to insert the optical fiber system 9 into the endoscope 2 to assemble the endoscope 2 and the optical fiber system 9. Thus, by using the first condition of the optical fiber system 9, the assembling of the imaging system 1 can be facilitated. Furthermore, when the assembled imaging system is inserted into the object 14, the optical fiber system 9 comprises the first condition to facilitate the insertion of the endoscope 2 into the object 14.

The optical fiber system 9 further comprises a transfer mechanism 13 which is adapted to transfer the optical fiber system from the second condition to the first condition by unfolding and to transfer the optical fiber system 9 from the first condition to the second condition by folding, wherein the unfolding and folding procedure is similar to that of an umbrella.

It is preferred to use a transfer mechanism which is known from so-called basket catheters. Such a transfer mechanism is, for example, disclosed in US 20060009690 A1.

The imaging system 1, for example, the coupling between the light source 4 and the illumination fiber bundles 10, is adapted to be able to address the different illumination fiber bundles individually. In particular, the light source 4, the coupling between the light source and the illumination fiber bundles 10 and the illumination fiber bundles 10 are adapted such that the illumination fiber bundles 10 illuminate the interior of the object 14 sequentially, i.e. that on the interior of the object sequentially different spatial light intensity distributions are generated.

In the following, a method for three-dimensional imaging of the interior of an object will be described with respect to FIG. 4.

After the start in step 101 the optical fiber system 9 is transferred to the second condition in which the fiber bundles 10, 11 are parallel to each other. In this condition, the optical fiber system 9 is inserted into the optical system insertion hole 12 in the endoscope 2. The step of inserting the optical fiber system 9 into the endoscope can be omitted, if the optical fiber system 9 is already located in the endoscope 2.

In step 103 the endoscope 2 comprising the optical fiber system 9 in the second condition is inserted into the object 14 and advanced to the position at which a three-dimensional image of the interior of the object 14 should be reconstructed.

After the end portion of the endoscope 2 has reached the desired position, the end portion of the optical fiber system 9, which has been inserted into the object 14, is unfolded by the transfer mechanism 13 in step 104, i.e. the optical fiber system 9 is transferred from the second condition to the first condition.

In step 105 the illumination fiber bundles 10 illuminate the interior of the object 14 sequentially, and the light, which is reflected from the interior of the object 14, is collected by the collecting fiber bundle 11. Thus, on the interior of the object different spatial light intensity distributions are sequentially generated and reflected different spatial light intensity distributions are acquired. The different spatial light intensity distributions, which have been collected by the collecting fiber bundle 11 are transferred to the detector 5, which is in this embodiment a CCD camera and which converts the light signals comprising the spatial light intensity distributions into electrical signals. The electrical signals, i.e. the spatial light intensity distributions, are transferred from the detector 5 to the reconstruction means 6, which is in this embodiment a reconstruction computer 6.

In step 106 the acquired spatial light intensity distributions are reconstructed into a three-dimensional image of the interior of the object 14 by reconstruction algorithms which are known, for example, from the above cited references. It is preferred that a three-dimensional image is reconstructed from the spatial light intensity distributions by shape-from-shading.

In step 107 the reconstructed three-dimensional image is displayed on the monitor 7 on which, for example, a surgeon can view the three-dimensional image of the interior of the object 14.

In step 108 it has to be decided, whether the steps of acquiring, reconstructing and viewing are to be continued or not. This decision can be made by the surgeon or by predetermined criteria. A predetermined criteria might be that the steps 105, 106 and 107 are repeated until a surgical procedure, which is carried out simultaneously, has been completed.

If in step 108 it has been decided, that the acquiring, reconstructing and viewing should stop, in step 109 the control unit 8 stops these processes and the end portion of the optical fiber system 9 is folded to the second condition, in which the fiber bundles are parallel to each other, i.e. the optical fiber system 9 is transferred from the first condition to the second condition. After that, in step 110, the endoscope 2 of the imaging system 1 comprising the optical fiber system 9 in the second condition is taken out from the body 14, and, in step 111, the method for three-dimensional imaging of the interior of an object is completed.

By carrying out the above described method for three-dimensional imaging of the interior of an object, it is possible to display three-dimensional images of the interior of the object in real time.

According to the invention, the optical fiber system can be inserted into a casing, e.g., flexible or rigid casing of an endoscope wherein the casing can only comprise the optical fiber system, or the casing can comprise the optical fiber system and additional instruments, for example, additional surgical instruments.

Instead of fiber bundles, single optical fibers can be used. For example, one collecting fiber and several illumination fibers can be used, which act similar to the above described case, in which one collecting fiber bundle and several illumination fiber bundles are used.

The above mentioned illumination fiber bundles or illumination fibers, respectively, and the above mentioned collecting fiber bundles or collecting fibers, respectively, can be used according to the invention, if they are adapted to generate different spatial light intensity distributions on the interior of the object and to acquire the different spatial light intensity distributions which have been reflected from the interior of the object.

Figure 4:
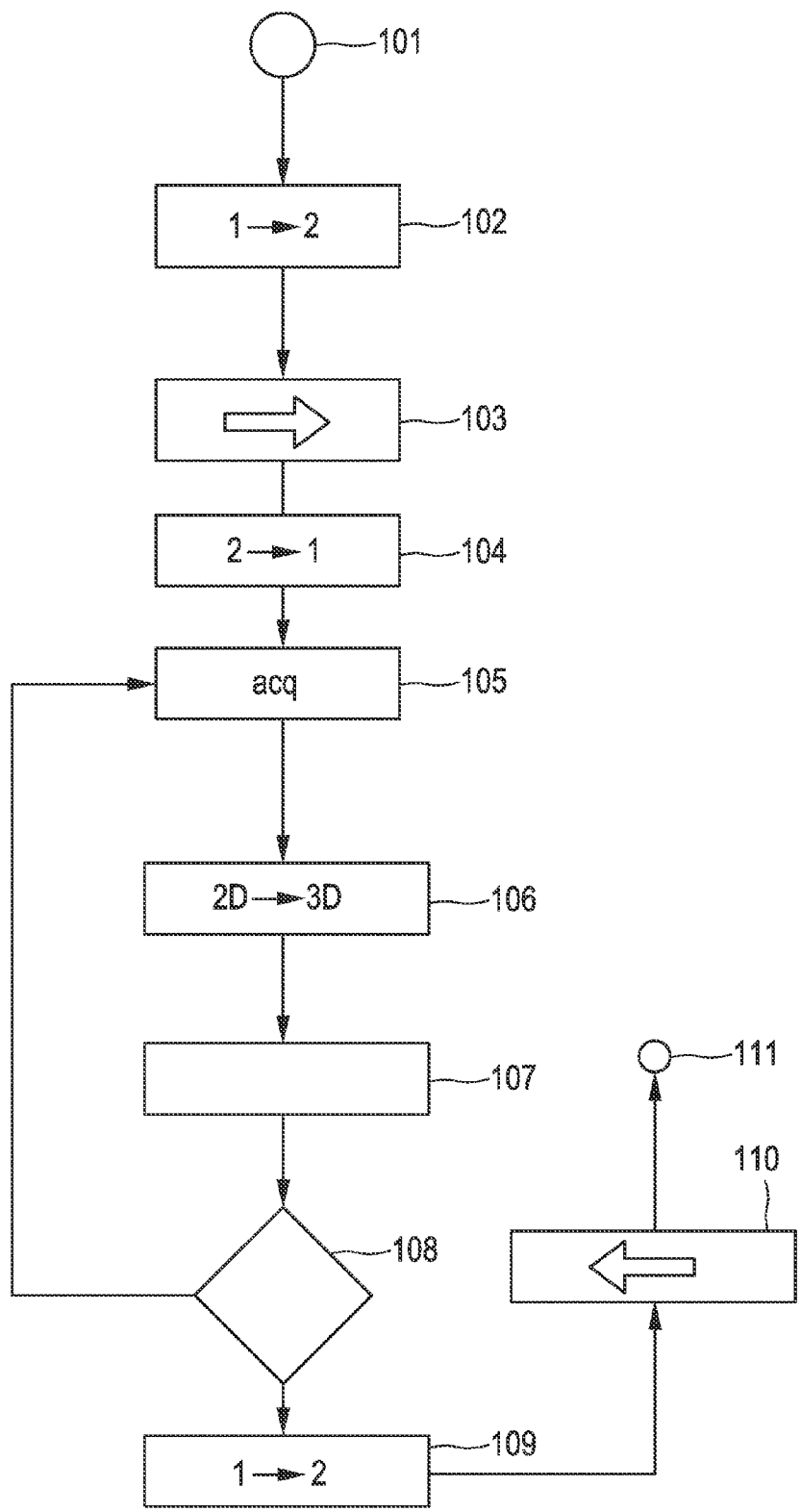
FIG. 4 shows a flowchart of a method for three-dimensional imaging of the interior of an object.

Is this preferred that the control unit 8 is adapted to control the imaging system according to the steps 104 to 109 of the imaging method of FIG. 4. In order to decide, whether the acquiring, reconstructing and viewing should stop, the control unit is preferentially connected to a further control unit of a surgical instrument, wherein the control unit of the imaging system decides to stop the acquiring, reconstructing and viewing, if it receives a signal from the control unit of the surgical instrument, which indicates that the surgical procedure has been stopped.

Figure 5:
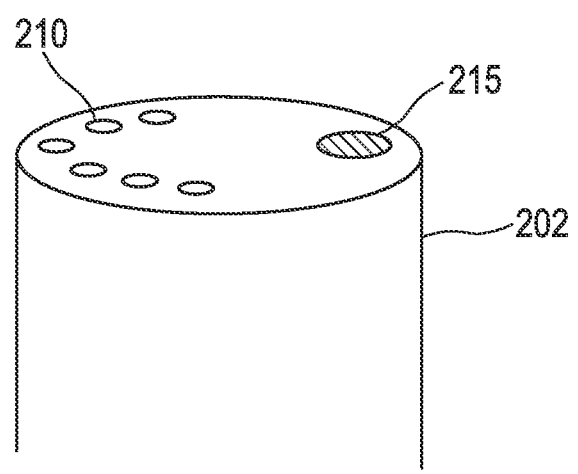
FIG. 5 shows schematically another embodiment of an imaging system according to the invention.

FIG. 5 shows an end portion of an endoscope 202 of another embodiment of an imaging system according to the invention. In this embodiment the illumination means comprises several illumination fibers or illumination fiber bundles 210, which are located within a casing 202, for example, an endoscope, and which are adapted to illuminate the interior of the object from different directions to generate different spatial light intensity distributions on the interior of the object. The detection means comprises in this embodiment a collecting fiber bundle 215, which is also located within the casing 202 and which is adapted to transfer collected light to a detector, for example, a CCD camera. In addition to or instead of the collecting fiber bundle 215 the detection means can comprise a camera, which is directly located on the tip of the casing 202, for example, on the tip of an endoscope.

In an embodiment according to the invention, also two or more detectors and/or collectors can be used and, at the same time, two or more illumination means to generate different spatial light intensity distributions on the interior of the object and to acquire the different spatial light intensity distributions, which have been reflected from the interior of the object.

In another embodiment of the invention, the imaging system comprises at least two endoscopes wherein at least one endoscope comprises the illumination means, and wherein at least one other endoscope comprises at least one detector and/or collector.

The invention claimed is:

1. An imaging system for three-dimensional imaging of the interior of an object comprising:
   an illumination system being adapted to illuminate the interior of the object with light, wherein the illumination system is capable of generating different spatial light intensity distributions on the interior of the object,
   a detection system adapted to detect the different spatial light intensity distributions,
   a reconstruction system adapted to reconstruct a three-dimensional image from the detected different spatial light intensity distributions,
   wherein the illumination system is adapted to illuminate the interior of the object from different directions by including an illuminator, moveable, in the three-dimensional space of the object, relative to the detection system,
   wherein the imaging system comprises an optical fiber system, which comprises at least one of a bundle of optical fibers of the illumination system and of the detection system and i) a first condition in which the optical fibers are arranged such that at least two of the optical fibers diverge from each other at an end portion of the bundle, and ii) a second condition in which the optical fibers are arranged such that the optical fibers are parallel to each other at said end portion of the bundle, wherein the optical fiber system comprises a transfer mechanism which is adapted to transfer the optical fiber system from one of the first and the second condition to the other of the first and the second condition.

2. The imaging system of claim 1, wherein the detection system comprises at least one of one single detector and one single collector.

3. The imaging system of claim 1, wherein the reconstruction system is adapted to reconstruct a three-dimensional image from the detected different spatial light intensity distributions by shape-from-shading.

4. The imaging system of claim 1, wherein the illumination system comprises several illuminators to illuminate the interior of the object from different directions to generate different spatial light intensity distributions on the interior of the object.

5. The imaging system of claim 1, wherein the illumination system comprises at least one optical fiber and a light source, wherein the detection system comprises at least one optical fiber and a detector, and wherein the optical fibers are arranged within a casing to transfer light from the light source to the interior of the object and to transfer light, which has been reflected from the interior, to the detector.

6. The imaging system of claim 5, wherein the illumination system comprises several optical fibers which are adaptable to illuminate the interior of the object from different directions to generate different spatial light intensity distributions on the interior of the object.

7. The imaging system of claim 5, wherein the illumination system comprises one illuminator comprising a light source and an optical fiber or a bundle of optical fibers, wherein the optical fiber or the bundle of optical fibers is moveable to illuminate the interior of the object from different directions to generate different spatial light intensity distributions on the interior of the object.

8. The imaging system of claim 5, wherein the optical fibers of the illumination system and of the detection system are located within the same casing in particular within a casing of the one endoscope.

9. The imaging system of claim 5, wherein the optical fibers of the illumination system and of the detection system are arranged to a bundle, wherein the at least one optical fiber of the detection system is located in the center of the bundle and wherein the optical fibers of the illumination system surround the at least one optical fiber of the detection system.

10. The imaging system of claim 1, wherein the transfer mechanism is adapted to at least one of unfold the optical fibers at said end portion of the bundle to transfer the optical fiber system from the second condition to the first condition and unfold the optical fibers at said end portion of the bundle to transfer the optical fiber system from the second condition to the first condition.

11. A method for three-dimensional imaging of the interior of an object by an imaging system, the method comprising:
illuminating the interior of the object with light by an illumination system, wherein the illumination system comprises an illuminator, moveable, in the three-dimensional space of the object, relative to a detection system, generating different spatial light intensity distributions on the interior of the object by illuminating the interior of the object in different directions, wherein the imaging system comprises an optical fiber system, which comprises at least one of a bundle of optical fibers of the illumination system and of the detection system in i) a first condition in which the optical fibers are arranged such that at least two of the optical fibers diverge from each other at an end portion of the bundle, or ii) a second condition in which the optical fibers are arranged such that the optical fibers are parallel to each other at said end portion of the bundle, wherein the optical fiber system comprises a transfer mechanism which is adapted to transfer the optical fiber system from one of the first and the second condition to the other of the first and the second condition,
detecting the different spatial light intensity distributions by the detection system,
reconstructing a three-dimensional image from the detected different spatial light intensity distributions.

12. The method of claim 11, wherein the light is detected by at least one of one single detector and collected by one single collector.

13. The method of claim 11, wherein a three-dimensional image is reconstructed from the detected different spatial light intensity distributions by shape-from-shading.

14. An imaging system for three-dimensional imaging of the interior of an object, comprising:
an illuminator moveable, in the three-dimensional space of the object to illuminate the interior of the object with light, wherein the illuminator generates different spatial light intensity distributions on the interior of the object by illuminating the interior of the object in different directions;
a detector to detect the different spatial light intensity distributions, wherein the illuminator is moveable in the three-dimensional space relative to the detector; and
a processor to reconstruct a three-dimensional image from the detected different spatial light intensity distributions,
wherein the imaging system comprises an optical fiber system, which comprises at least one of a bundle of optical fibers of the illumination system and of the detection system and i) a first condition in which the optical fibers are arranged such that at least two of the optical fibers diverge from each other at an end portion of the bundle, and ii) a second condition in which the optical fibers are arranged such that the optical fibers are parallel to each other at said end portion of the bundle, wherein the optical fiber system comprises a transfer mechanism which is adapted to transfer the optical fiber system from one of the first and the second condition to the other of the first and the second condition.

* * * * *